(12) United States Patent
Leo et al.

(10) Patent No.: US 8,894,589 B2
(45) Date of Patent: Nov. 25, 2014

(54) MEDICAL APPARATUS SYSTEM HAVING OPTICAL FIBER LOAD SENSING CAPABILITY

(75) Inventors: Giovanni Leo, Chene Bougeries (CH); Nicolas Aeby, Geneva (CH); Daniele Inaudi, Lugano (CH)

(73) Assignee: Endosense SA, Geneva (CH)

( * ) Notice: Subject to any disclaimer, the term of this patent is extended or adjusted under 35 U.S.C. 154(b) by 2009 days.

(21) Appl. No.: 11/989,902

(22) PCT Filed: Aug. 1, 2006

(86) PCT No.: PCT/IB2006/002090
§ 371 (c)(1),
(2), (4) Date: Nov. 22, 2010

(87) PCT Pub. No.: WO2007/015139
PCT Pub. Date: Feb. 8, 2007

(65) Prior Publication Data
US 2011/0087112 A1    Apr. 14, 2011

Related U.S. Application Data

(63) Continuation-in-part of application No. 11/237,053, filed on Sep. 28, 2005, now Pat. No. 8,182,433.

(60) Provisional application No. 60/704,825, filed on Aug. 1, 2005.

(51) Int. Cl.
| | | |
|---|---|---|
| A61B 5/103 | (2006.01) | |
| A61B 5/02 | (2006.01) | |
| A61B 5/00 | (2006.01) | |
| A61B 17/00 | (2006.01) | |
| A61B 19/00 | (2006.01) | |
| A61B 18/14 | (2006.01) | |

(52) U.S. Cl.
CPC ... *A61B 5/02007* (2013.01); *A61B 2017/00039* (2013.01); *A61B 2019/5261* (2013.01); *A61B 18/1492* (2013.01); *A61B 5/6885* (2013.01); *A61B 2017/00084* (2013.01); *A61B 19/46* (2013.01); *A61B 2019/2211* (2013.01); *A61B 5/0084* (2013.01); *A61B 2017/00053* (2013.01); *A61B 2019/465* (2013.01); *A61B 19/2203* (2013.01); *A61B 2562/0266* (2013.01); *A61B 2019/547* (2013.01); *A61B 2019/442* (2013.01); *A61B 2019/448* (2013.01)
USPC .......................................... 600/587; 600/478

(58) Field of Classification Search
USPC ................................... 600/587, 478
See application file for complete search history.

(56) References Cited

U.S. PATENT DOCUMENTS

| | | | |
|---|---|---|---|
| 4,757,194 A | 7/1988 | Simms | |
| 4,873,989 A | 10/1989 | Einzig | |

(Continued)

FOREIGN PATENT DOCUMENTS

| | | |
|---|---|---|
| DE | 30 20 785 | 12/1981 |
| DE | 38 28 550 | 3/1990 |

(Continued)

OTHER PUBLICATIONS

Application and File History for U.S. Appl. No. 13/447,813, filed Apr. 16, 2012, inventors Leo et al.

(Continued)

*Primary Examiner* — Max Hindenburg
*Assistant Examiner* — Renee Danega
(74) *Attorney, Agent, or Firm* — Dykema Gossett PLLC

(57) ABSTRACT

Apparatus is provided for diagnosing or treating an organ or vessel, wherein a device having at optical fiber contact force sensors disposed in a distal extremity thereof and a deflection mechanism configured to deflect the elongate body at a location proximal of the distal extremity. The optical fiber contact force sensors are configured to be coupled to processing logic programmed which computes a force vector responsive to detected changes in the optical characteristics of the optical fiber contact force sensors arising from deflection of the distal extremity resulting from contact with the tissue of the wall of the organ or vessel.

14 Claims, 9 Drawing Sheets

(56) References Cited

U.S. PATENT DOCUMENTS

| | | |
|---|---|---|
| 4,918,492 A | 4/1990 | Fedinand et al. |
| 4,966,597 A | 10/1990 | Cosman |
| 4,983,034 A | 1/1991 | Spillman, Jr. |
| 5,014,709 A | 5/1991 | Bjelkhagen et al. |
| 5,018,529 A | 5/1991 | Tenerz et al. |
| 5,065,010 A | 11/1991 | Knute |
| 5,104,392 A | 4/1992 | Kittrell et al. |
| 5,122,137 A | 6/1992 | Lennox |
| 5,178,153 A | 1/1993 | Einzig |
| 5,201,317 A | 4/1993 | Kanazawa et al. |
| 5,202,939 A | 4/1993 | Belleville et al. |
| 5,248,305 A | 9/1993 | Zdrahala |
| 5,279,793 A | 1/1994 | Glass |
| 5,289,256 A | 2/1994 | Gramling |
| 5,321,501 A | 6/1994 | Swanson et al. |
| 5,321,510 A | 6/1994 | Childers et al. |
| 5,348,019 A | 9/1994 | Sluss, Jr. et al. |
| 5,392,117 A | 2/1995 | Belleville et al. |
| 5,396,887 A | 3/1995 | Imran |
| 5,409,000 A | 4/1995 | Imran |
| 5,423,807 A | 6/1995 | Milder |
| 5,446,546 A | 8/1995 | Breidenbach et al. |
| 5,575,787 A | 11/1996 | Abela et al. |
| 5,594,819 A | 1/1997 | Narendran et al. |
| 5,633,494 A | 5/1997 | Danisch |
| 5,645,065 A | 7/1997 | Shapiro |
| 5,662,108 A | 9/1997 | Budd et al. |
| 5,688,267 A | 11/1997 | Panescu et al. |
| 5,696,863 A | 12/1997 | Kleinerman |
| 5,769,847 A | 6/1998 | Panescu et al. |
| 5,772,590 A | 6/1998 | Webster, Jr. |
| 5,782,828 A | 7/1998 | Chen et al. |
| 5,798,521 A | 8/1998 | Froggatt |
| 5,807,265 A | 9/1998 | Itoigawa et al. |
| 5,833,688 A | 11/1998 | Sieben et al. |
| 5,844,927 A | 12/1998 | Kringlebotn |
| 5,859,717 A | 1/1999 | Scopey et al. |
| 5,904,658 A | 5/1999 | Niederauer et al. |
| 5,906,614 A | 5/1999 | Stern et al. |
| 5,967,978 A | 10/1999 | Littmann et al. |
| 6,039,743 A | 3/2000 | Quiachon et al. |
| 6,056,436 A | 5/2000 | Sirkis et al. |
| 6,063,078 A | 5/2000 | Wittkampf |
| 6,066,130 A | 5/2000 | Gregory et al. |
| 6,088,088 A | 7/2000 | Fortenberry |
| 6,102,926 A | 8/2000 | Tartaglia et al. |
| 6,113,590 A | 9/2000 | Fischer et al. |
| 6,113,593 A | 9/2000 | Tu et al. |
| 6,120,476 A | 9/2000 | Fung et al. |
| 6,120,520 A | 9/2000 | Saadat et al. |
| 6,129,667 A | 10/2000 | Dumoulin et al. |
| 6,133,593 A | 10/2000 | Boos et al. |
| 6,134,003 A | 10/2000 | Tearney et al. |
| 6,171,275 B1 | 1/2001 | Webster, Jr. |
| 6,173,091 B1 | 1/2001 | Reich |
| 6,175,669 B1 | 1/2001 | Colston et al. |
| 6,197,023 B1 | 3/2001 | Muntermann |
| 6,210,346 B1 | 4/2001 | Hall et al. |
| 6,217,574 B1 | 4/2001 | Webster |
| 6,226,542 B1 | 5/2001 | Reisfeld |
| 6,246,898 B1 | 6/2001 | Vesely et al. |
| 6,256,090 B1 | 7/2001 | Chen et al. |
| 6,262,822 B1 | 7/2001 | Obhi et al. |
| 6,266,542 B1 | 7/2001 | Stern et al. |
| 6,266,551 B1 | 7/2001 | Osadchy et al. |
| 6,272,371 B1 | 8/2001 | Shlomo |
| 6,276,215 B1 | 8/2001 | Berg |
| 6,310,990 B1 | 10/2001 | Putnam et al. |
| 6,324,918 B1 | 12/2001 | Gitis et al. |
| 6,370,412 B1 | 4/2002 | Armoundas et al. |
| 6,398,778 B1 | 6/2002 | Gu et al. |
| 6,425,894 B1 | 7/2002 | Brucker et al. |
| 6,451,009 B1 | 9/2002 | Dasilva et al. |
| 6,458,123 B1 | 10/2002 | Brucker et al. |
| 6,466,811 B1 | 10/2002 | Hassett |
| 6,470,205 B2 | 10/2002 | Bosselmann et al. |
| 6,470,286 B1 | 10/2002 | Seip et al. |
| 6,471,710 B1 | 10/2002 | Bucholtz |
| 6,546,271 B1 | 4/2003 | Reisfeld |
| 6,547,780 B1 | 4/2003 | Sinofsky |
| 6,558,378 B2 | 5/2003 | Sherman et al. |
| 6,563,970 B1 | 5/2003 | Bohnert et al. |
| 6,572,804 B2 | 6/2003 | Randall et al. |
| 6,602,242 B1 | 8/2003 | Fung et al. |
| 6,660,001 B2 | 12/2003 | Gregory |
| 6,674,928 B2 | 1/2004 | Johnson et al. |
| 6,695,808 B2 | 2/2004 | Tom |
| 6,701,931 B2 | 3/2004 | Sliwa, Jr. et al. |
| 6,852,109 B2 | 2/2005 | Winston et al. |
| 6,868,195 B2 | 3/2005 | Fujita |
| 6,898,338 B2 | 5/2005 | Kersey et al. |
| 6,915,048 B2 | 7/2005 | Kersey et al. |
| 6,947,637 B2 | 9/2005 | Smith |
| 6,955,675 B2 | 10/2005 | Jain |
| 6,986,769 B2 | 1/2006 | Nelson et al. |
| 7,050,662 B2 | 5/2006 | Behrmann et al. |
| 7,114,938 B2 | 10/2006 | Chou |
| 7,173,713 B2 | 2/2007 | Xu et al. |
| 7,241,986 B2 | 7/2007 | Wang |
| 7,460,964 B2 | 12/2008 | Mizota et al. |
| 7,466,879 B2 | 12/2008 | Tjin |
| 7,491,957 B2 | 2/2009 | Kitamura et al. |
| 7,903,907 B1 | 3/2011 | Park et al. |
| 8,075,498 B2 | 12/2011 | Leo et al. |
| 8,157,789 B2 | 4/2012 | Leo et al. |
| 2001/0021843 A1 | 9/2001 | Bosselmann |
| 2002/0041722 A1 | 4/2002 | Johnson |
| 2002/0041723 A1 | 4/2002 | Ronnekleiv et al. |
| 2002/0057859 A1 | 5/2002 | Walter et al. |
| 2002/0072680 A1 | 6/2002 | Schock et al. |
| 2004/0082844 A1 | 4/2004 | Vardi et al. |
| 2004/0165810 A1 | 8/2004 | Fujita |
| 2004/0206365 A1 | 10/2004 | Knowlton |
| 2004/0243119 A1 | 12/2004 | Lane et al. |
| 2005/0062979 A1 | 3/2005 | Zhu et al. |
| 2005/0213870 A1 | 9/2005 | Kersey et al. |
| 2006/0013523 A1 | 1/2006 | Childlers et al. |
| 2006/0045408 A1 | 3/2006 | Jones et al. |
| 2006/0100610 A1 | 5/2006 | Wallace et al. |
| 2006/0133715 A1 | 6/2006 | Belleville et al. |
| 2006/0200049 A1 | 9/2006 | Leo et al. |
| 2006/0263002 A1 | 11/2006 | Pocha et al. |
| 2007/0014490 A1 | 1/2007 | Silverbrook et al. |
| 2007/0041019 A1 | 2/2007 | Schmidt |
| 2007/0043338 A1 | 2/2007 | Moll et al. |
| 2007/0060847 A1 | 3/2007 | Leo et al. |
| 2007/0065077 A1 | 3/2007 | Childers et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2007/0265503 A1 | 11/2007 | Schlesinger et al. |
| 2008/0009750 A1 | 1/2008 | Aeby et al. |
| 2008/0294144 A1 | 11/2008 | Leo et al. |
| 2009/0138007 A1 | 5/2009 | Govari et al. |
| 2009/0177095 A1 | 7/2009 | Aeby et al. |
| 2009/0287092 A1 | 11/2009 | Leo et al. |
| 2009/0306643 A1 | 12/2009 | Pappone et al. |
| 2009/0306650 A1 | 12/2009 | Govari et al. |
| 2010/0063478 A1 | 3/2010 | Selkee |
| 2010/0087835 A1 | 4/2010 | Blumenkranz et al. |
| 2010/0094163 A1 | 4/2010 | Deladi et al. |
| 2010/0328675 A1 | 12/2010 | Bertholds et al. |
| 2012/0078138 A1 | 3/2012 | Leo et al. |
| 2012/0265102 A1 | 10/2012 | Leo et al. |

FOREIGN PATENT DOCUMENTS

| | | |
|---|---|---|
| EP | 0 281 405 | 9/1988 |
| EP | 0 934 728 | 8/1999 |
| EP | 1909650 | 4/2008 |
| EP | 2 047 797 | 4/2009 |
| JP | 09297078 | 11/1997 |
| JP | 10137200 | 5/1998 |
| JP | 2000227367 | 8/2000 |

(56) References Cited

FOREIGN PATENT DOCUMENTS

| | | |
|---|---|---|
| JP | 2004251779 | 9/2004 |
| WO | WO9729678 | 8/1997 |
| WO | WO 97/32182 | 9/1997 |
| WO | WO 97/38637 | 10/1997 |
| WO | WO 98/19044 | 5/1998 |
| WO | WO 99/45994 | 9/1999 |
| WO | WO 01/33165 | 5/2001 |
| WO | WO01/33165 | 5/2001 |
| WO | WO 01/74252 | * 10/2001 |
| WO | WO 02/19898 | 3/2002 |
| WO | WO 02/19903 | 3/2002 |
| WO | WO 02/23148 | 3/2002 |
| WO | WO 02/47751 | 6/2002 |
| WO | WO2004/002303 | 1/2004 |
| WO | WO 2005/059510 | 6/2005 |
| WO | WO 2006/092707 | 9/2006 |
| WO | WO 2007/015139 | 2/2007 |
| WO | WO2007/015139 | 2/2007 |
| WO | WO 2007/050960 | 5/2007 |
| WO | WO 2007/111737 | 10/2007 |
| WO | WO 2008/000246 | 1/2008 |
| WO | WO 2008/003307 | 1/2008 |
| WO | WO 2008/045958 | 4/2008 |
| WO | WO 2009/114955 | 9/2009 |

OTHER PUBLICATIONS

European Office Action for European Application No. 11158967.7-1654 dated Mar. 12, 2013.
Notification of the Second Chinese Office Action for Chinese Application No. 200980125027.0 dated Mar. 12, 2013. English Translation is provided.
European Office Action for European Application No. 08826173.0-1265 dated Oct. 1, 2012.
European Office Action for European Application No. 06795186.3-2310 dated Oct. 18, 2012.
Notification of the First Office Action of Chinese Office Action for Chinese Application No. 200980125027.0 dated Jun. 29, 2012.
European Office Action from European Application No. 09746251.9 dated Jan. 24, 2012.
Japanese Interrogatory for Japanese Application No. 2007/557615 dated Oct. 29, 2012.
Japanese Notification of Reasons for Rejection for Japanese Application No. 2011509074 dated May 28, 2013.
Written Opinion and International Searching Authority for International Application No. PCT/US2012/033791 dated Aug. 13, 2012.
Application and File History for U.S. Appl. No. 13/096,647, filed Apr. 28, 2011, inventor Leo.
Application and File History for U.S. Appl. No. 13/179,076, filed Jul. 8, 2011.
Non-final Office Action dated Jun. 22, 2011 for U.S. Appl. No. 11/450,072.
European Office Action for European Application No. 06710474.5 dated Feb. 16, 2009.
European Office Action for European Application No. 06710474.5 dated Aug. 24, 2009.
Application and File History for U.S. Appl. No. 12/127,657, filed May 27, 2008, inventor Leo.
Application and File History for US Publication No. 2006/0200049 published Sep. 7, 2006, inventor Leo.
Application and File History for US Publication No. 2008/0009750 published Jan. 10, 2008, inventor Leo.
Application and File History for US Publication No. 2008/0294144 published Nov. 27, 2008, inventor Leo.
Application and File History for US Publication No. 2009/0177095 published Jul. 9, 2009, inventor Leo.
Application and File History for US Publication No. 2009/0287092 published Nov. 19, 2009, inventor Leo.
Application and File History for US Publication No. 2007/0060847 published Mar. 15, 2007, inventor Leo.

Zhang et al., "On SDM/WDM FBG Sensor Net for Shape Detection of Endoscope," Proceedings of the IEEE International Conference on Mechatronics & Automation, Jul. 2005.
Endosense receives CE mark for Tacticath force-sensing ablation catheter, May 4, 2009.
Endosense launches TOCCATA clinical study Oct. 7, 2008.
"Endosense achieves ISO 13485 certification" Aug. 12, 2008.
"Endosense unveils five groundbreaking abstracts on contact force measurement for catheter ablation" May 13, 2008.
Fuster et al., "ACC/AHA/ESC 2006 Guidelines for the Management of Patients with Atrial Fibrillation," Circulation Journal of the Americal Heart Association, 2006, Dallas, Texas, pp. e319-e321.
Calkins et al., "HRS/EHRA/ECAS Expert Consensus Statement on Catheter and Surgical Ablation of Atrial Fibrillation: Recommendations for Personnel, Policy, Procedures and Follow-Up," Europace (2007.
Natale et al., "Venice Chart Internatinoal Consensus Document on Atrial Fibrillation Ablation," Journal of Cardiovascular Electrophysiology, vol. 18. No. 5, May 2007.
Cappato et al., "Worldwide Survey on the Methods, Efficacy, and Safety of Catheter Ablation for Human Atrial Fibrillation," Journal of the Americal Heart Association, 2005.
Hasin et al., "Miniature Force Transducer for Myocardial Stimulation and Local Tension Measurements," IEEE Transactions on Biomedical Engineering, vol. BME-26, No. 2, Feb. 1979.
"Sensei X Robotic Catheter System for Electrophysiology Procedures," MedGadget, Sep. 18, 2009.
Xiao et al., "Fiber optic pressure sensor with self-compensation capability for harsh environment applications," Optical Engineering May 2005, vol. 44(5).
International Search Report, dated Sep. 11, 2007.
International Search Report, dated Feb. 5, 2008.
International Search Report, dated Dec. 13, 2006.
Notice of Reasons for Rejection (translation) from Japanese Application No. 2007-557615 mailing date: Sep. 13, 2011.
International Preliminary Report on Patentability and Written Opinion from International Application No. PCT/IB2009/051967 date of issuance Nov. 17, 2010.
U.S. Appl. No. 12/127,657, filed May 27, 2008, Giovanni et al.
U.S. Appl. No. 12/352,426, filed Jan. 12, 2009, Aeby et al.
U.S. Appl. No. 12/152,473, filed May 14, 2008, Giovanni et al.
Office Action from U.S. Appl. No. 11/753,429 dated May 10, 2011.
International Search Report (PCT/IB2009/051967), dated Mar. 16, 2010.
International Search Report (PCT/IB2008/002675), dated Dec. 2, 2009.
Office Action of related application (U.S. Appl. No. 11/237,053), dated Apr. 12, 2010.
Office Action (Restriction Requirement) of related application (U.S. Appl. No. 11/436,926), dated May 22, 2010.
Office Action of related application (U.S. Appl. No. 11/753,429), dated Feb. 19, 2010.
FISO, "FOS-N Strain Sensor," FISO Technologies Inc., (2006), Canada.
Dickmann, "Experiment 03, Fabry Perot Resonator," (2003), pp. 1-19.
Precision Photonics Corporation, "Basic Physics and Design of Etalons," (2003), pp. 1-5.
Luna Innovations, "EFPI Techniques for Strain and Displacement Sensing," (Aug. 1999).
Luna Innovations, "Fiber Optic Bragg Grating Sensor," www.lunainnovations.com/products/shape.asp, (Aug. 2005).
Meller, "Extrinsic Fabry-Perot Interferometer System Using Wavelength Modulated Source," (Dec. 1996).
FISO Technologies, "Technical Note, Principle of Fiber-Optic Sensors," (received prior to Feb. 20, 2007).
Uffelen, "Anchoring points for fibre optic strain sensors," Optical Techniques for Smart Structures and Structural Monitoring, (Feb. 1997), London, UK.
Lo, "Using in-fiber Bragg-grating sensors for measuring axial strain and temperature simultaneously on surfaces of structures," Optical Engineering, (Aug. 1998) vol. 37, Issue 8, pp. 2272-2276.

(56) References Cited

OTHER PUBLICATIONS

Dupont, "DuPont Zenite LCP liquid crystal polymer resin," Product and Property Guide, K-15415, May 2006.
European Office Action from European Application No. 06795186.3 dated Aug. 9, 2011.
European Office Action from European Application No. 11158967.7 dated Aug. 10, 2011.
IPRP and Written Opinion for International Application No. PCT/US2012/033791 dated Oct. 24, 2013.
European Office Action for European Application No. 11158967.7-1654 dated Aug. 13, 2013.
Chinese Office Action for Chinese Application No. 200980125027.0 dated Oct. 10, 2013.
U.S. Appl. No. 12/127,657, filed May 27, 2008, Leo.
U.S. Appl. No. 11/989,902, filed Feb. 1, 2008, Leo et al.
U.S. Appl. No. 12/127,657.
U.S. Appl. No. 11/989,902.
Barb, Matthew et al., "Versatile, High-Speed Force Transducer Using a Laser Diode Beam as an Optical Lever," Journal of Applied Physiology, 88(1):308-314, 2000.
Barret, M.D. et al., "Extrinsic Fabry-Perot Interometer for Measuring the Stiffness of Ciliary Bundles on Hair Cells," IEEE Transactions on Biomedical Engineering, 46(3):331-9, Mar. 1999.
Del Villar, Ignacio et al., "Optimization of Sensitivity in Long Period Fiber Gratings with Overlay Deposition," Optic Express, 13(1):56-69, Jan. 10, 2005.
Erdemir, A. et al., "Fiberoptic Measurement of Tendon Forces is Influenced by Skin Movement Artifact," Journal of Biomechanics, 36(3):449-55, vol. 36, No. 3, Mar. 2003.
Fearn, L.A. et al.,"An Optical Fiber Transducer for Single Myofibril Force Measurement," IEEE Transactions on Biomedical Engineering, 40(11):1127-32, Nov. 1993.
Inaudi, D. Application of opticl Fiber sensor in civil structural monitoring. Proceedings of the SPIE—the International Society for Optical Engineering: SPIE—In. Soc. Opt.Eng., 4328: 1-7, tableau 1, USA, 2001.
Komi, P.V. et al., "Optic Fibre as a Transducer of Tendomuscular Forces," European Journal of Applied Physiology and Occupational Physiology, 72(3):278-80, 1996.
Paris-Seeley, N.F. et al., "A Compliance-Independent Pressure Transducer for Biomedical Device-Tissue Interfaces," Biomedical Instrumentation & Technology, 34(6):432-31, Nov.-Dec. 2000.
Rao, YJ. Recent progress in application of in-fibre Bragg grating sensors. Optics and Lasers in Engineering, 31(4):297-324, Elsevier, UK, Apr. 1999.
Schmidt, Markus et al., "Fiber-Optic Extrnisic Fabry-Perot Interoferometer Strain Sensor with <50pm Displacement Resolution Using Three-Wavelength Digital Phase Demodulation," Optic Express, Apr. 9, 2001.
International Search Report (PCT/IB 2010/000021), dated May 27, 2010.
Peirs et al., "Design of an Optical Force Sensor for Force Feedback during Minimally Invasive Robotic Surgery".
Notification of the First Office Action for Chinese Application No. 20068007106.8 dated May 8, 2009.
Fernandez et al., "Multi-component force sensor based on multiplexed Fibre Bragg grating strain sensors" Measurement Science and Technology (2001) 810-813.
European Office Action for European Application No. 06795186.3 dated Nov. 25, 2010.
Yokoyama, MD, et al., "Novel Radiofrequency Ablation Catheter with Contact Force Sensor Predicts Lesion Size and Incidence of Steam Pop in Canine Model," Heart Rhythm Society, May 2007, Denver USA, vol. 4, Issue 5.
Shah et al., "Evaluation of a New Catheter Sensor for Real-Time Measurement of Tissue Contact," Heart Rhythm Society, May 2006, Boston, USA, vol. 3, Issue 5.
"The Unique Force Sensor Ablation Catheter," www.endosense.com/site/product.htm, Mar. 2007.
Application and File History for U.S. Appl. No. 11/237,053, filed Sep. 28, 2005, inventor Leo.
Application and File History for U.S. Appl. No. 11/436,926, filed May 15, 2006, inventor Leo.
Peirs et al., "A micro optical force sensor for force feedback during minimally invasive robotic surgery," Sensors and Actuators A 115 (2004) 447-455.
Brown, Anthony Wayne, "Development of a Brillouin Scattering Based Distributed Fiber-Optic Strain Sensor" Ph.D. Thesis Abstract, The University of New Brunswick, 2001.
Hansen Medical, "Intellisense Fine Force Technology", http://www.hansenmedical.com/products/intellisense.aspx, accessed Sep. 22, 2009, 1 pg.
Hansen Medical, "Sensei Robotic Catheter System", product brochure, 2010.
Hansen Medical, "Artisan Extend Control Catheter", product brochure, 2009.
NTT Innovative Technology, Fiber-Optic Strain-Monitoring Technology: BOTDR (Brillouin Optical Time-Domain Refitometer), http://www.ntt-tec.jp/en/technology/C316html, accessed Jul. 18, 2005, 2 pgs.
Park et al, "Force Sensing Robot Fingers Using Embedded Fiber Bragg Grating Sensors and Shape Deposition Manufacturing", 2007 IEEE conference on Robotics and Automotion, Apr. 10-14, 2007.
Application and File History for U.S. Appl. No. 13/308,196, filed Nov. 30, 2011, inventors Leo et al.

* cited by examiner

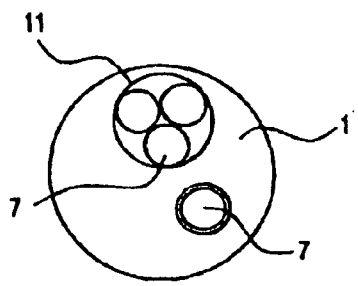
FIG. 15
FIG. 16
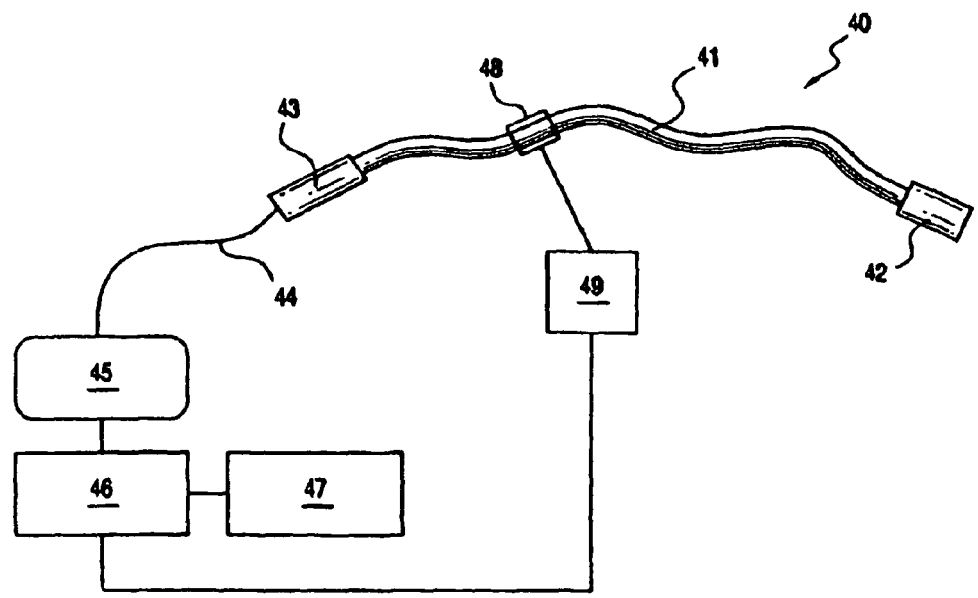

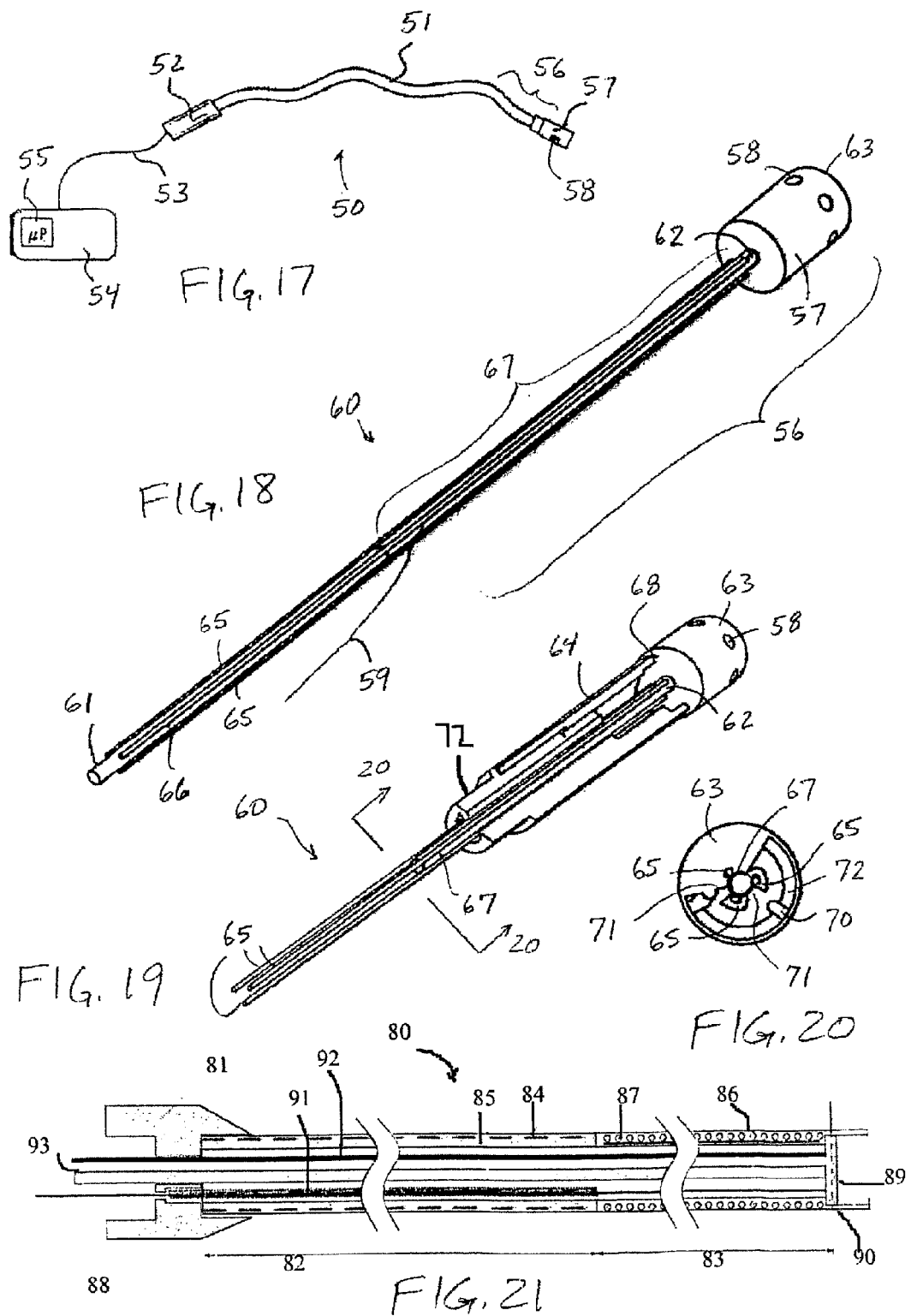

MEDICAL APPARATUS SYSTEM HAVING OPTICAL FIBER LOAD SENSING CAPABILITY

This application is a 371 application based upon International application no. PCT/IB2006/002090, filed 1 Aug. 2006 (the '090 application), now completed; which claims priority to U.S. application Ser. No. 11/436,926, filed 15 May 2006 (the '926 application), now U.S. Pat. No. 8,075,498; which is a continuation-in-part of U.S. application Ser. No. 11/237,053, filed 28 Sep. 2005 (the '053 application), now U.S. Pat. No. 8,182,433; which claims the benefit of priority to U.S. application No. 60/704,825, filed 1 Aug. 2005 (the '825 application). The '090 application, '926 application, '053 application, and '825 application are each hereby incorporated by reference as though fully set forth herein.

FIELD OF THE INVENTION

The present invention relates to apparatus for exploring and treating an organ that permits computation of a multi-dimensional force vector resulting from contact between the distal extremity of the apparatus and the tissue of the wall of the organ.

BACKGROUND OF THE INVENTION

For many years, exploration and treatment of various organs or vessels has been possible using catheter-based diagnostic and treatment systems. Such catheters are introduced through a vessel leading to the cavity of the organ to be explored or treated or alternatively may be introduced directly through an incision made in the wall of the organ. In this manner, the patient avoids the trauma and extended recuperation times typically associated with open surgical procedures.

To provide effective diagnosis or therapy, it is frequently necessary to first map the zone to be treated with great precision. Such mapping may be performed, for example, when it is desired to selectively ablate current pathways within a heart to treat atrial fibrillation. Often, the mapping procedure is complicated by difficulties in locating the zone(s) to be treated due to periodic movement of the heart throughout the cardiac cycle.

Previously-known systems for mapping the interior of a vessel or organ are described, for example, in U.S. Pat. Nos. 6,546,271 and 6,226,542. The catheters described in those patents employ electro-magnetic, magnetic or acoustic sensors to map the position of a distal end of the catheter in space and then construct a three-dimensional visualization of the vessel or organ interior.

One drawback of such previously known mapping systems is that they rely on manual feedback of the catheter and/or impedance measurements to determine when the catheter is properly positioned in the vessel or organ. Those systems do not measure contact forces with the vessel or organ wall or detect contact forces applied by the catheter against the organ or vessel wall that may modify the true wall location. Instead, previously known mapping methods are time-consuming, dependent upon the skill of the clinician, and cannot compensate for artifacts created by excessive contact forces.

It therefore would be desirable to provide apparatus and methods for detecting and monitoring contact forces between a mapping catheter and the wall of the organ or vessel to permit faster and more accurate mapping. It also would be desirable to provide apparatus and methods that permit the process to be automated, thereby improving registration of measured electro-physiologic values and spatial coordinates, for example, by recording such values only where the contact forces fall within a predetermined range.

Once the topography of the vessel or organ is mapped, either the same or a different catheter may be employed to effect treatment. Depending upon the specific treatment to be applied to the vessel or organ, the catheter may comprise any of a number of end effectors, such as RF ablation electrodes, a rotary cutting head, laser ablation system, injection needle or cryogenic fluid delivery system. Exemplary systems are described, for example, in U.S. Pat. Nos. 6,120,520, 6,102,926, 5,575,787, 5,409,000 and 5,423,807.

Because the effectiveness of such end effectors often depends having the end effector in contact with the tissue of the wall of the organ or vessel, many previously-known treatment systems include expandable baskets or hooks that stabilize the distal extremity of the catheter in contact with the tissue. Such arrangements, however, may be inherently imprecise due to the motion of the organ or vessel. Moreover, the previously-known systems do not provide the ability of sense the load applied to the distal extremity of the catheter by movement of the tissue wall.

For example, in the case of a cardiac ablation system, at one extreme the creation of a gap between the end effector of the treatment system and the tissue wall may render the treatment ineffective, and inadequately ablate the tissue zone. At the other extreme, if the end effector of the catheter contacts the tissue wall with excessive force, if may inadvertently puncture the tissue, resulting in cardiac tamponade.

In view of the foregoing, it would be desirable to provide a catheter-based diagnostic or treatment system that permits sensing of the load applied to the distal extremity of the catheter, including periodic loads arising from movement of the organ or tissue. It further would be desirable to have a load sensing system coupled to control operation of the end effector, so that the end effector is operated, either manually or automatically, only when the contact force is detected to fall within a predetermined range.

U.S. Pat. No. 6,695,808 proposes several solutions to measure the force vector arising from contact with the tissue surface, including mechanical, capacitive, inductive and resistive pressure sensing devices. One drawback of such devices, however, is that they are relatively complex and must be sealed to prevent blood or other liquids from disturbing the measurements. In addition, such load sensing devices may result in an increase in the insertion profile of the distal extremity of the catheter. Still further, sensors of the types described in that patent may be subject to electromagnetic interference.

One previously-known solution for dealing with potential electromagnetic interference in the medical environment is to use light-based systems rather than electrical measurement systems, such as described in U.S. Pat. No. 6,470,205 to Bosselman. That patent describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer. Calculation of the bend angles does not require knowledge of the characteristics of the rigid links.

International Publication No. WO 01/33165 to Bucholtz describes an alternative spatial orientation system wherein wavelength changes measured in a triad of optical fiber strain sensors are used to compute the spatial orientation of a catheter or other medical instrument. Although the publication discloses that the strain sensors may be encased within a deformable sheath, as in Bosselman, calculation of the bend angles is not described as requiring characterization of the material properties of the deformable sheath.

Accordingly, it would be desirable to provide diagnostic and treatment apparatus, such as a catheter or guide wire, that permits sensing of loads applied to a distal extremity of the apparatus, but which do not substantially increase the insertion profile of the apparatus.

It further would be desirable to provide diagnostic and treatment apparatus, such as a catheter and guide wire, that permits computation of forces applied to a distal extremity of the apparatus, and which are substantially immune to electromagnetic interference.

It still further would be desirable to provide a diagnostic and treatment apparatus, such as catheter system, that permits computation of forces applied to a distal extremity of the catheter that is substantially immune to environmental conditions encountered during use of the catheter, such as exposure to body fluids and the presence of room-to-body temperature gradients.

SUMMARY OF THE INVENTION

The present invention generally comprises diagnostic or treatment apparatus that permits sensing of the load applied to a distal extremity of apparatus, including periodic loads arising from movement of the organ or tissue.

The apparatus and methods of the present invention permit detection and monitoring of contact forces between an interventional apparatus, such as a mapping catheter or guide wire, and the wall of the organ or vessel to facilitate the speed and accuracy of such mapping.

The present invention also includes apparatus and methods that enable a mapping or treatment process to be automated, thereby improving registration of measured electro-physiologic values and spatial coordinates, for example, by recording such values only where the contact forces fall within a predetermined range.

Apparatus constructed in accordance with the present invention may include a load sensing system coupled to control operation of an end effector of a diagnostic or treatment apparatus, so that the end effector is operated, either manually or automatically, only when the contact force is detected to fall within a predetermined range.

Apparatus in accordance with this invention also may comprise diagnostic and treatment apparatus that permit sensing of loads applied to a distal extremity of the apparatus, but which do not substantially increase the insertion profile of the apparatus.

Diagnostic and treatment apparatus in accordance with this invention also enable computation of forces applied to a distal extremity of the apparatus, and which are substantially immune to electromagnetic interference and/or environmental conditions encountered during use of the catheter, such as exposure to body fluids and the presence of room-to-body temperature gradients.

This invention also provides apparatus for use in a hollow-body organ, such as the heart, that permits sensing of loads applied to a distal extremity of the apparatus during movement of the organ, so as to optimize operation of an end effector disposed within the distal extremity.

Apparatus constructed in accordance with the present invention comprises medical apparatus, such as catheter, having at least two optical fiber sensors disposed in a distal extremity configured to deform responsive to contact forces, and a deflection mechanism disposed in the catheter configured to deflect the elongate body at a location proximal of the distal extremity. The inventive apparatus also may comprise processing logic programmed to compute at least a two-dimensional force vector responsive to detected changes in the optical characteristics of the optical fiber sensors. The apparatus of the present invention may be configured as a catheter or guide wire, or may be employed in other medical apparatus where knowledge of tissue contact forces is desired.

More preferably, the apparatus of the present invention comprises three optical fiber sensors disposed within the distal extremity so that they are not co-planar. For example, the three optical fiber sensors may be arranged at the apices of an equilateral triangle centered on the geometric axis of the apparatus, although other configurations also may be employed. Use of three such optical fiber sensors advantageously permits the computation of a three-dimensional force vector. The optical fiber sensors preferably are chosen from among a Fiber Bragg Grating (FBG), an Intrinsic Fabry-Perot Interferometer (IFPI), an Extrinsic Fabry-Perot Interferometer (EFPI), a Long Period Grating (LPG), a two, three or four arm Michelson interferometer (MI), a Brillouin scattering strain sensor, or intensity-based fiber optic strain sensor.

Further in accordance with the present invention, the apparatus includes processing logic, such as programmed general purpose microprocessor or application specific integrated circuit, operatively coupled to receive an output signal from the optical fiber sensors, and to compute a two- or three-dimensional force vector from that output signal, depending upon the number of optical fiber sensors employed. The processing logic may be programmed with a matrix of values associated with physical properties of an individual device, and applies those values to the detected changes in wavelength to compute the external forces applied to the distal extremity. More preferably, a force-strain conversion matrix specific for each device is determined during manufacture, and that force-strain conversion is associated with the device via an appropriate memory device, label or tag.

In accordance with the one aspect of the present invention, two optical fiber sensors may be used provided that the neutral axis of the distal extremity of the apparatus is well characterized. More preferably, three optical fiber sensors are disposed within the distal extremity to allow deformations (elongation or contraction) imposed on the deformable body to be measured at three or more non-planar points.

The extremely small dimensions of the optical fiber sensors provide ample space in the distal extremity of the apparatus to house for other diagnostic or treatment devices. When configured as a catheter or guide wire, the device has a substantially reduced insertion profile relative to previously-known systems having force-sensing capability. In addition, the optical nature of the sensors ensures that the possible presence of liquids does not disturb the measurements, and ensures a high degree of immunity from electromagnetic interference.

The apparatus of the present invention optionally may include any of a number of previously-known end effectors disposed in the distal extremity for treating a vessel or organ, for example, an electrode to measure an electric potential (e.g., to perform an endocavity electrocardiogram), an electrode configured to ablate tissue by deposition of radiofrequency energy, an irrigation channel, and/or a three-dimensional positioning sensor.

Advantageously, the load sensing system of the present invention may be employed to continuously monitor deflection of a distal extremity. For example, the signal output by the load sensing system may be used to guide or control the use and operation of an end effector of a catheter either manually or automatically. Illustratively, when employed as part of an electrophysiology mapping catheter, the present invention permits electrical potentials of the tissue to be measured only at contact positions where the contact force applied to the distal extremity of the catheter by the tissue wall falls within a predetermined range. Such an arrangement not only offers to improve spatial registration between the mapped values and tissue location, but also makes possible the use of robotic systems capable of automating the mapping process. As a further example, the output of the load sensing system may be used to control operation of a treatment end effector, for example, to position the end effector in contact with the organ wall and to energize the ablation electrode only when the contact force is detected to fall within a predetermined range.

In addition, the distal part of at least one of the optical fibers, or an additional optical fiber, extends beyond the others and is equipped with an additional FBG, LPG, IFPI, EFPI or Brillouin scattering type sensor to permit the temperature of the distal extremity to be monitored.

Alternatively, or in addition, a temperature sensor may be disposed in the distal extremity in close proximity to the optical fiber sensors. Temperatures measured by the temperature sensor may be used to compensate for deformations of the deformable body arising from temperature variations, which might otherwise erroneously be interpreted as force-related deformations. The temperature sensor may comprise any of a number of temperature sensors. More specifically, the temperature sensor comprises an additional optic fiber that is not constrained to deform in unison with the distal extremity, but instead is free to expand due to temperature variations. In a preferred embodiment, the temperature sensor comprises an additional FBG, LPG, IFPI, EFPI or Brillouin scattering type optical fiber sensor.

The additional optical fiber also could extend beyond the other optical fibers and include an additional FBG, LPG, IFPI, EFPI or Brillouin scattering type sensor to measure the temperature of the distal extremity. Alternatively, the distal part of the additional fiber extends beyond the other optical fibers in the distal extremity and includes a temperature sensor comprising a Michelson interferometer sensor or an intensity sensor.

In accordance with a preferred alternative embodiment, the apparatus may comprise an electrophysiology catheter comprising an elongated portion, a distal extremity, and a proximal end. An irrigation tube extends from the proximal end to the distal extremity and has a plurality of optical fibers arranged symmetrically around its circumference. The optical fibers include sensors, such as Bragg Gratings, disposed near the distal extremity. In accordance with one aspect of the invention, the irrigation tube in the vicinity of the distal extremity comprises a flexible tube having a low thermal expansion coefficient which reduces sensor artifacts introduced by environmental effects, such a temperature fluctuations.

BRIEF DESCRIPTION OF THE DRAWINGS

Further features of the invention, its nature and various advantages will be more apparent from the accompanying drawings and the following detailed description of the preferred embodiments, in which:

FIG. 15 is a schematic plan view of the distal extremity including a fourth optical fiber;

FIG. 16 is a schematic view of apparatus of the present invention wherein the output of the load sensing system is utilized to control automated operation of the apparatus;

FIG. 17 is a schematic view of an alternative embodiment of apparatus of the present application;

FIG. 18 is a perspective view of a distal subassembly of the apparatus of FIG. 17;

FIG. 19 is a perspective view of the distal subassembly of FIG. 18 including a protective housing, which is partially cut-away;

FIG. 20 is a cross-sectional view of the distal subassembly of FIG. 19 taken along line 20-20; and FIG. 21 is a perspective view of an exemplary deflectable catheter shaft for use with the distal subassembly of FIG. 19.

DETAILED DESCRIPTION OF THE INVENTION

The present invention involves medical apparatus and methods for use with diagnostic and treatment systems wherein it is desired to measure contact forces between a distal extremity of the apparatus and a tissue wall of an organ or vessel. The load sensing capability of the present invention may be used intermittently to measure the contact forces at discrete points, or alternatively, used to continuously monitor contact forces to assist in manipulation and operation of the apparatus.

Medical apparatus incorporating the present invention illustratively may be configured as catheters or guide wires to be manually manipulated by a clinician, with the clinician using a visual or audio cue output by the load sensing system to determine, for example, optimum position for measuring an electrophysiologic value or performing treatment. Alternatively, the medical apparatus may be robotically controlled, with the load sensing system of the present invention providing a feedback and control system.

Advantageously, medical apparatus equipped with the load sensing system of the present invention are expected to permit faster, more accurate diagnosis or treatment of a vessel of organ, with improved registration between measured values and spatial locations. For example, a catheter with the inventive load sensing system would permit mapping of cardiac electrical potentials by providing reproducible contact forces between the distal extremity of the catheter and the tissue wall, thereby making the results of the mapping process less dependent on the skill of the individual clinician and facilitating automated procedures.

Figure 1:
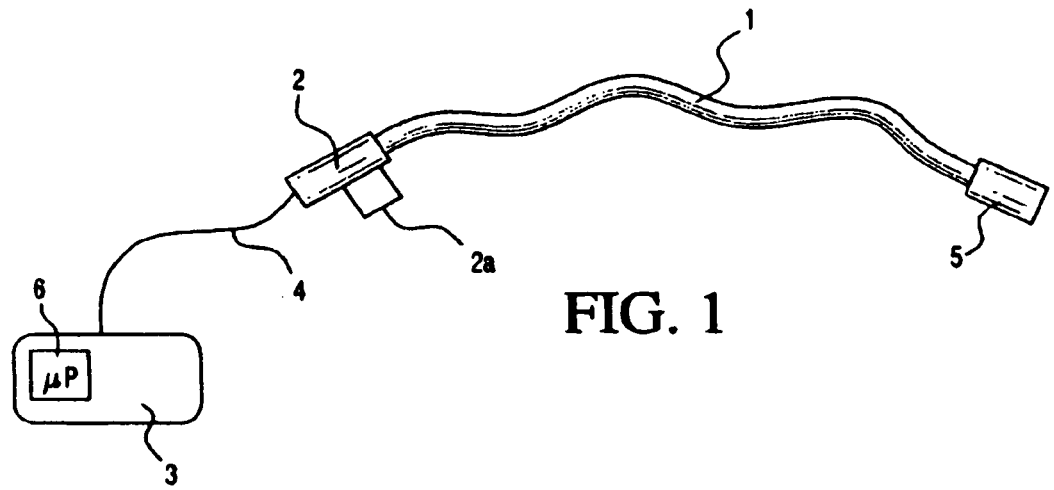
FIG. 1 is a schematic view of apparatus according to the invention.
Figure 2:
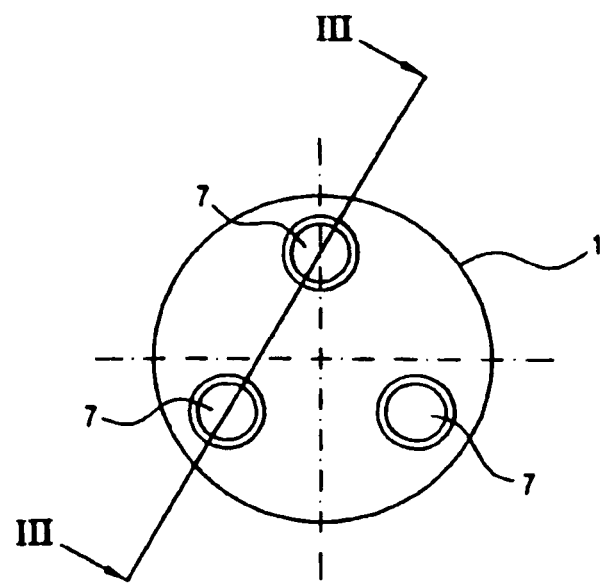
FIG. 2 is a schematic plan view of the distal extremity of FIG. 1.

Referring now to FIGS. 1 and 2, exemplary apparatus constructed in accordance with the principles of the present invention comprises catheter 1 having proximal end 2 coupled to console 3 via cable 4. As described in detail below, catheter 1 includes distal extremity 5 that illustratively carries any one or more of a number of end effectors known in the art for diagnosing or treating a vessel or organ. While the present invention is described in the context of a catheter system for cardiac mapping and ablation, it will be understood that medical apparatus constructed in accordance with the present invention advantageously may be used for other purposes, such as delivering drugs or bioactive agents to a vessel or organ wall or performing transmyocardial revascularization or cryo-ablation, such as described in the above-referenced patents.

Proximal end 2 preferably includes storage device 2a, such as a memory chip, RFID tag or bar code label, which stores data that may be used in computing a multi-dimensional force vector, as described herein after. Alternatively, storage device 2a need not be affixed to proximal end 2, but instead could be a separate item, e.g., packaging, individually associated with each catheter. Proximal end 2 may be manipulated manually or automatically to cause a desired amount of articulation or flexion of distal extremity 5 using any of a number of deflection mechanisms that are known in the art, such as pull wires or suitably configured electroactive polymers. In accordance with one aspect of the present invention, the deflection mechanism is disposed in the catheter body so that it causes articulation or deflection of the catheter at a location proximal of the distal extremity. Catheter 1 may be advanced, retracted and turned manually or automatically.

Distal extremity 5 of catheter 1 comprises a deformable body having at least two optical fiber sensors that extend proximally and are coupled to console 3 via proximal end 2 and cable 4. More preferably, catheter 1 includes three optical fiber sensors disposed therein. In addition, control signals to and from the end effector(s) in distal extremity 5 are transmitted via suitable components of cable 4 to console 3, to a tactile component of proximal end 2. As will be apparent, the nature of cable 4 depends on the nature of the end effectors disposed in distal extremity 5 of catheter 1.

Console 3 comprises electronic and optical components to drive the optical fiber sensors and to interpret the output signals therefrom. Console 3 further includes processing logic 6, such as a programmed general purpose microprocessor or application-specific integrated circuit, which receives an output signal corresponding to wavelength changes manifested in the optical fiber sensors due to forces applied to the distal extremity of the deformable body. Processing logic 6 computes a multi-dimensional force vector based upon that output signal and a matrix of physical characteristics of the individual deformable body, as described in detail below. Console 3 preferably also includes means to manifest an output from the load sensing system, such as a visual display or an auditory device. Alternatively, console 3 may output a signal for display on a separate monitor.

Figure 3:
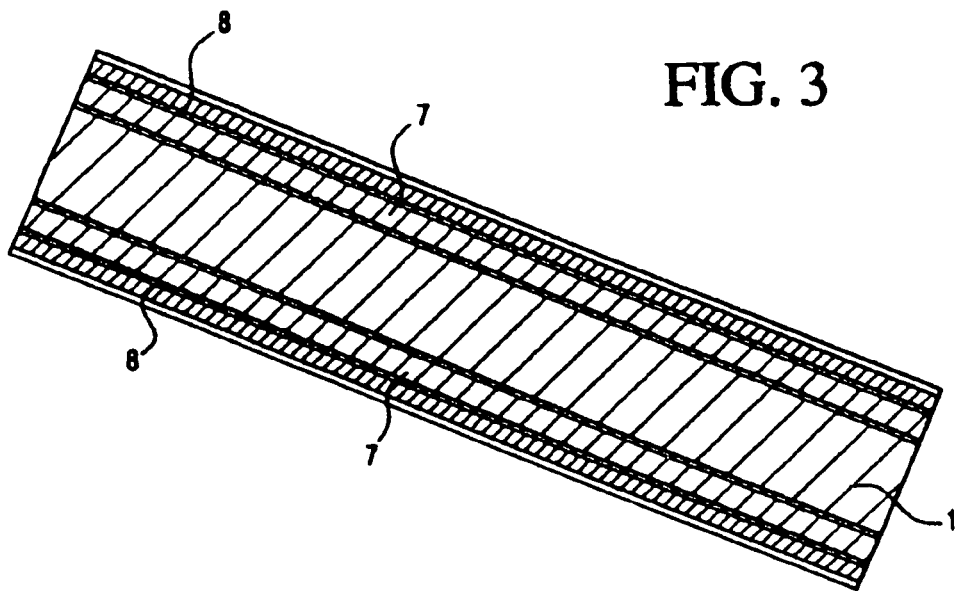
FIG. 3 is a section according to of FIG. 2.

Referring now to FIGS. 2 and 3, catheter 1 preferably has at least two optical fiber sensors 7 disposed within it, so that deformation of distal extremity 5 is transferred to the sensors 7. Two optical fiber sensors may be employed so long as the location of the neutral axis of the distal extremity is known or determined during manufacture. More preferably, distal extremity 1 includes at least three optical fiber sensors, and comprises a molded, machined or extruded material, such as typically are used in making guide wires or catheters. To ensure that the optical fibers form an integral part of catheter 1, the optical fibers may be affixed within the distal extremity using adhesive or other means as, for example, overmolding or co-extrusion. In FIG. 3, optical fibers 7 are glued into distal extremity 5 using adhesive 8.

Preferably, catheter 1 comprises a liquid crystal polymer ("LCP") that has a small positive or even negative coefficient of thermal expansion in the direction of extrusion. A variety of liquid crystal polymers are known in the art, and such materials may be coated with PARYLENE or a metallic coating to enhance resistance to fluid absorption.

Where three optical fiber sensors are employed, optical fibers 7 are disposed in distal extremity 5 so that the optical fiber sensors are not co-planar, i.e., are not situated in a single plane. Illustratively, the optical fibers are disposed at the apices of an equilateral triangle centered on the longitudinal axis of the catheter. Other configurations are possible, so long as optical fibers experience different degrees of bending and elongation during deformation of distal extremity 5. Optical fiber sensors 7 may be chosen from among a Fiber Bragg Grating (FBG), a Long Period Grating (LPG), an Intrinsic Fabry-Perot Interferometer (IFPI), an Extrinsic Fabry-Perot Interferometer (EFPI), a two, three or four arm Michelson interferometer (MI), a Brillouin scattering strain sensor, or intensity-based fiber optic strain sensor.

Figure 4:
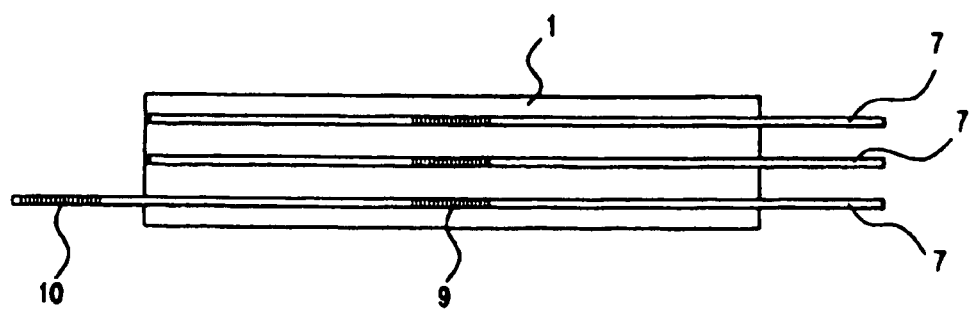
FIG. 4 is a schematic view of the side of the distal extremity showing the disposition of the Fiber Bragg Grating (FBG) or Long Period Grating (LPG) sensors.

Referring now to FIG. 4, catheter 1 is depicted housing three optical fibers 7 having FBG or LPG strain sensors 9 disposed in distal extremity 5. An FBG sensor is an interferometer in which a stable Bragg grating is permanently impressed (e.g., photo-etched) into the core of the fiber. The region of periodic variation in the index of refraction of the fiber core acts as a very narrowband reflection filter that reflects light having a predetermined Bragg wavelength. Light therefore is reflected from the FBG in a narrow spike with a center wavelength that is linearly dependent on the Bragg wavelength and the mean index of refraction of the core. Consequently, deformations that alter the grating characteristics result in a shift in the reflected Bragg wavelength.

An LPG is similar in construction to an FBG, and comprises a single mode fiber having periodic index modulation of the refractive index of the fiber core with a much longer period than an FBG. Use and operation of a catheter employing LPGs rather than FBGs is similar to that described below.

During use of the apparatus, the distal extremity of catheter 1 is compressed and bent due to loads imposed by contacting the tissue of the organ. The portions of optical fibers 7 that are situated in the distal extremity also are deformed but in a varying degrees according to their respective positions in the distal extremity. In addition, the distal extremity may be deflected by deflecting a more proximal portion of the catheter using any of a variety of previously-known catheter deflection mechanisms, such as described in U.S. Pat. No. 4,960,134 to Webster, which is incorporated herein by reference. In this case, the apparatus will compute the force with which the distal extremity contacts the tissue of the organ or vessel.

The initial calibration of the FBG sensors, i.e., the average wavelength reflected from the Bragg grating in the absence of any applied forces (referred to as the "Bragg wavelength") is determined from grating characteristics impressed during manufacture of the optical fiber. Any deviations from the Bragg wavelength are proportionately related to an exact parameter, such as strain. In the embodiment of FIG. 4, the Bragg grating allows the deformation (elongation or contraction) of each of optical fibers 7 to be quantified by measuring the change in wavelength of the light reflected by the Bragg grating.

The foregoing information, together with known physical properties of the distal extremity of the catheter, enable processing logic 6 of console 3 to calculate the components of a multidimensional force vector with appropriate algorithms. The force vector then may be displayed or otherwise manifested, for example, as a graphic on a display screen or by varying the pitch emitted from an auditory device housed in or associated with console 3.

Still referring to FIG. 4, one of optical fibers 7 preferably extends beyond the others and includes second FBG (or LPG) 10 for measuring the temperature of the front end of the distal extremity. Temperature changes at the front end of the distal extremity may arise, e.g., due to operation of an ablation electrode, and will cause a change in the associated Bragg wavelength. By knowing the physical properties of the fiber and measuring the wavelength of the light reflected by the grating, processing logic 6 may compute the temperature at the level of the distal extremity, for example, to monitor tissue ablation progress.

Referring again to FIG. 1, console 3 comprises a laser, preferably a tunable laser diode, arranged to inject a beam of light into the optical fibers through cable 4, and a photodetector that detects variations in the characteristics of the reflected light beam due to deformations imposed on the strain sensors and distal extremity 5. Preferably, console 3 includes a Fiber Bragg Grating Demodulator.

In such a system, each of the optical fiber sensors has a Bragg grating with a different wavelength, and which therefore responds in a specified range of frequency. A tunable laser is coupled to all of the optical fiber sensors and scans a certain frequency several times per second. A photodiode records the wavelength change for each Bragg grating when the frequency of the laser centers on the grating frequency. In this manner, each of the optical fiber sensors may be interrogated as the tunable laser scans through the grating frequencies of the sensors.

Further in accordance with the principles of the present invention, processing logic 6 is programmed to compute a two- or three-dimensional force vector from the output of the Fiber Bragg Grating Demodulator. The theory underlying these computations is now described.

For apparatus having three fiber optic Bragg strain sensors embedded within the distal extremity of the catheter, the total strain may be computed using:

$$\begin{bmatrix} \varepsilon_{1,t} \\ \varepsilon_{2,t} \\ \varepsilon_{3,t} \\ \Delta T_t \end{bmatrix} = \begin{bmatrix} C_\varepsilon & 0 & 0 & C_{\varepsilon T} \\ 0 & C_\varepsilon & 0 & C_{\varepsilon T} \\ 0 & 0 & C_\varepsilon & C_{\varepsilon T} \\ 0 & 0 & 0 & C_T \end{bmatrix} \cdot \left( \begin{bmatrix} \lambda_{1,t} \\ \lambda_{2,t} \\ \lambda_{3,t} \\ \lambda_{4,t} \end{bmatrix} - \begin{bmatrix} \lambda_{1,r} \\ \lambda_{2,r} \\ \lambda_{3,r} \\ \lambda_{4,r} \end{bmatrix} \right) \quad (1.1)$$

$$\varepsilon_t = C \cdot (\lambda_t - \lambda_r) \quad (1.1a)$$

Where:
r—time when reference (zero) measurement is set
t—time relative to reference time
$\lambda_{i,r}$, i=1,4—reference wavelengths of Bragg-gratings
$\lambda_{i,t}$, i=1,4—wavelengths of Bragg-gratings at time t
$\varepsilon_{i,t}$, i=1,3—total strain values at time t
$\Delta T_t$—Temperature change at time t
$C_\varepsilon$—coefficient of linearity between the wavelength and strain
$C_{\varepsilon T}$—coefficient of temperature compensation of the Bragg-grating
$C_T$—coefficient of linearity between the wavelength and temperature
$\lambda_r$—Matrix (vector) of Bragg-gratings reference wavelengths
$\lambda_t$—Matrix (vector) of Bragg-gratings wavelengths at time t
$\varepsilon_t$—Matrix (vector) of total strain and temperature changes
C—Strain transducer and compensation matrix The total strain includes a component due to thermal expansion of the distal extremity arising from the difference between the measured temperature of the distal extremity and a predetermined reference temperature. The elastic strain, which is a function of the applied force, therefore may be calculated using:

$$\begin{bmatrix} \varepsilon_{el1,t} \\ \varepsilon_{el2,t} \\ \varepsilon_{el3,t} \end{bmatrix} = \begin{bmatrix} 1 & 0 & 0 & -\alpha_{Tc} \\ 0 & 1 & 0 & -\alpha_{Tc} \\ 0 & 0 & 1 & -\alpha_{Tc} \end{bmatrix} \cdot \begin{bmatrix} \varepsilon_{1,t} \\ \varepsilon_{2,t} \\ \varepsilon_{3,t} \\ \Delta T_t \end{bmatrix} \quad (1.2)$$

$$\varepsilon_{el,t} = \alpha_T \cdot \varepsilon_t \quad (1.2a)$$

Where:
$\varepsilon_{eli,t}$, i=1,3—elastic strain values at time t
$\alpha_T$—Thermal expansion coefficient of catheter material
$\varepsilon_{el,t}$—Matrix (vector) of elastic strain at time t
$\alpha_T$—Temperature reduction matrix $$(1.1a)\hat{}(1.2a) \Rightarrow \varepsilon_{el,t} = \alpha_T \cdot C \cdot (\lambda_t - \lambda_r) \quad (1.3)$$

The elastic strains are related to the internal forces experienced by the optical fiber sensors as a function of both the physical dimensions of, and the material properties of, the distal extremity:

$$\begin{bmatrix} \varepsilon_{el1,t} \\ \varepsilon_{el2,t} \\ \varepsilon_{el3,t} \end{bmatrix} = \begin{bmatrix} 1 & y_1 & -x_1 \\ 1 & y_2 & -x_2 \\ 1 & y_3 & -x_3 \end{bmatrix} \cdot \begin{bmatrix} \frac{1}{E_{ten} \cdot A} & 0 & 0 \\ 0 & \frac{1}{E_{flex} \cdot I_x} & 0 \\ 0 & 0 & \frac{1}{E_{flex} \cdot I_y} \end{bmatrix} \cdot \begin{bmatrix} N_{z,t} \\ M_{x,t} \\ M_{y,t} \end{bmatrix} \quad (2.1)$$

$$\varepsilon_{el,t} = G \cdot \delta \cdot I_{F,t} \quad (2.1a)$$

Where:
$x_i$ and $y_i$, i=1,3—coordinates of Bragg-gratings with respect to center of gravity of the catheter cross-section
$E_{ten}$—Equivalent tension/compression Young modulus of catheter
$E_{flex}$—Equivalent flexural Young modulus of catheter
$I_x$—Moment of inertia with respect to x axis
$I_y$—Moment of inertia with respect to y axis
$N_{z,t}$—Normal force in direction of z axis at time t
$M_{x,t}$—Bending moment with respect to x axis at time t $M_{y,t}$—Bending moment with respect to y axis at time t
G—Geometry matrix
δ—Matrix of flexibility
$I_{F,t}$—Matrix (vector) of internal forces at time t Equation (2.1) may be rearranged to solve for the internal forces as a function of the elastic strain. The elastic strain from equation (1.3) may then be substituted into the rearranged matrix system to compute the internal forces as a function of the elastic strain, as shown in Equation (2.3) below:

$$(2.1) \Rightarrow \begin{bmatrix} N_{z,t} \\ M_{x,t} \\ M_{y,t} \end{bmatrix} = \begin{bmatrix} E_{ten} \cdot A & 0 & 0 \\ 0 & E_{flex} \cdot I_x & 0 \\ 0 & 0 & E_{flex} \cdot I_y \end{bmatrix} \cdot \begin{bmatrix} 1 & y_1 & -x_1 \\ 1 & y_2 & -x_2 \\ 1 & y_3 & -x_3 \end{bmatrix}^{-1} \cdot \begin{bmatrix} \varepsilon_{el1,t} \\ \varepsilon_{el2,t} \\ \varepsilon_{el3,t} \end{bmatrix} \quad (2.2)$$

$$(2.1a) \Rightarrow I_{F,t} = S \cdot G^{-1} \cdot \varepsilon_{el,t} \quad (2.2a)$$

Where: $S = \delta^{-1}$—Stiffness matrix $$(1.3)\hat{\ }(2.1a) \Rightarrow I_{F,t} = S \cdot G^{-1} \cdot \alpha_T \cdot C \cdot (\lambda_t - \lambda_r) \quad (2.3)$$

It remains only to relate the internal forces experienced by the optical fiber sensors to the external contact forces actually exerted on the distal extremity by the tissue wall. These forces are computed based on the positions of the optical fiber sensors from the exterior wall of the distal extremity, assuming the catheter material is substantially incompressible:

$$\begin{bmatrix} F_{x,t} \\ F_{y,t} \\ F_{z,t} \end{bmatrix} = \begin{bmatrix} 0 & 0 & -\frac{1}{d} \\ 0 & \frac{1}{d} & 0 \\ -1 & 0 & 0 \end{bmatrix} \cdot \begin{bmatrix} N_{z,t} \\ M_{x,t} \\ M_{y,t} \end{bmatrix} \quad (3.1)$$

$$F_t = d \cdot I_{F,t} \quad (3.1a)$$

Where:
$F_{x,t}$—Touching external transversal force at time t, in direction of x axis (with opposite sense)
$F_{y,t}$—Touching external transversal force at time t, in direction of y axis (with opposite sense)
$F_{z,t}$—Touching external normal force at time t, in direction of z axis (with opposite sense, compression is positive)
d—distance between the touching point of lateral forces and the cross-section with sensors (along z axis)
$F_t$—Matrix of touching external forces at time t
d—Matrix of conversion $$(2.3)\hat{\ }(3.1a) \Rightarrow F_t = d \cdot S \cdot G^{-1} \cdot \alpha_T \cdot C \cdot (\lambda_t - \lambda_r) \quad (3.2)$$

$$F_t = K_\lambda \cdot (\lambda_t - \lambda_r) = K_\lambda \cdot \lambda_t - F_r \quad (3.3)$$

Where:

$K_\lambda$—Force transducer matrix, $K_\lambda = d \cdot S \cdot G^{-1} \cdot \alpha_T \cdot C$ \quad (3.4)

$F_r$—Reference force matrix (vector), $F_r = K_\lambda \cdot \lambda_r$ \quad (3.5)

Solution of equations (3.1) to (3.5) provides the normal and transverse forces applied to the external surface of the distal extremity, i.e., $F_{norm,t} = F_{z,t}$ and $F_{trans,t}$ = square root ($F^2_{x,t} + F^2_{y,t}$). The angle $\gamma_t$ of application of the transverse force may be computed from Table I:

TABLE I

| $F_{x,t}$ | $F_{y,t}$ | $\gamma_t$ |
|---|---|---|
| ≥0 | ≥0 | $\arcsin(F_{y,t}/F_{tran,t})$ |
| <0 | ≥0 | $\Pi - \arcsin(F_{y,t}/F_{tran,t})$ |
| <0 | <0 | $\Pi - \arcsin(F_{y,t}/F_{tran,t})$ |
| ≥0 | <0 | $2*\Pi + \arcsin(F_{y,t}/F_{tran,t})$ |

Many of the values employed in equations (1.1) to (3.5) are related to the material properties of the distal extremity or optical fiber sensors, such as the Bragg wavelengths, thermal expansion coefficients and elastic moduli. Other values, such as the distances between the optical fiber sensors and the external surface of the distal extremity may be subject to variations as a consequence of the manufacturing process employed.

To ensure the accuracy of the computed force vector, specific information for each catheter may be stored in storage device 2a. Generally, the information make take the form of a data file that is input to console 3 prior to use of the catheter. For example, storage device 2a may comprise a memory chip associated with cable 4 in which such information is stored, or a bar code or a RFID tag located on proximal end 2 of the catheter or the packaging for the catheter. Alternatively, data specific to an individual catheter may be uploaded to console 3 from an item of removable storage (e.g., CD) or via secure download from the manufacturer's website.

The information specific to each catheter may be obtained during a calibration step, conducted during manufacture of the catheter, by subjecting the distal extremity of the catheter to a series of known forces. In this case, the foregoing equations may be collapsed so the normal and transverse forces may be computed directly from a force-to-wavelength conversion matrix:

$$F(t) = K(\lambda(t) - \lambda_0) \quad (4.0)$$

where:
F(t) is the vector of forces $[F_{x,t}, F_{y,t}, F_{z,t}]$,
λ(t) is the vector of wavelengths $[\lambda_{1,t}, \lambda_{2,t}, \lambda_{3,t}]$ measured for the individual sensors,
$\lambda_0$ is the vector of wavelengths $[\lambda^0_1, \lambda^0_2, \lambda^0_3]$ measured for the individual sensors with zero applied force, and
K is a matrix computed when the distal extremity is subjected to the series of known forces.

During the calibration step of manufacture, the catheter is subjected to the following forces in series: (1) a purely axial force of known magnitude F'; (2) a lateral force of known magnitude F''; and (3) a lateral force of known magnitude F''' applied 90 degrees to the orientation of force F''. When all of the forces F', F'', F''' and wavelengths are known, the force-to-strain conversion matrix K may be computed as:

$$K = F(\lambda(t) - \lambda_0)^{-1} \quad (5.0)$$

or:

$$\begin{bmatrix} F_x & F'_x & F''_x \\ F_y & F'_y & F''_y \\ F_z & F'_z & F''_z \end{bmatrix} \begin{bmatrix} (\lambda_1 - \lambda^0_1) & (\lambda'_1 - \lambda^0_1) & (\lambda''_1 - \lambda^0_1) \\ (\lambda_2 - \lambda^0_2) & (\lambda'_2 - \lambda^0_2) & (\lambda''_2 - \lambda^0_2) \\ (\lambda_3 - \lambda^0_3) & (\lambda'_3 - \lambda^0_3) & (\lambda''_3 - \lambda^0_3) \end{bmatrix}^{-1} = \quad (5.1)$$

$$\begin{bmatrix} a_{11} & a_{13} & a_{13} \\ a_{21} & a_{22} & a_{23} \\ a_{31} & a_{32} & a_{33} \end{bmatrix}$$

Force-to-strain conversion matrix K then may be stored in storage device 2a associated with the corresponding device, as described herein above. The values of the force-to-conversion matrix then may be input to console 3 when the catheter is coupled to the console using a bar code reader, input pad or direct electrical connection through cable 4. Once matrix K is provided for a given distal extremity, the normal force, transverse force and angle of application of the transverse force may be computed as described above and using Table I.

The values for the normal force, transverse force and angle of application of the transverse force, computed as described above, may be output as numerical values to a display monitor that forms part of console 3 or which is associated with console 3. In addition, a graphic including a variable size or colored arrow may be displayed pointing at a position on the circumference of a circle to visualize the magnitude and direction of the transverse force applied to the distal extremity. By monitoring this display, the operator may continuously obtain feedback concerning the contact forces applied to the distal extremity of the catheter.

Figure 5:
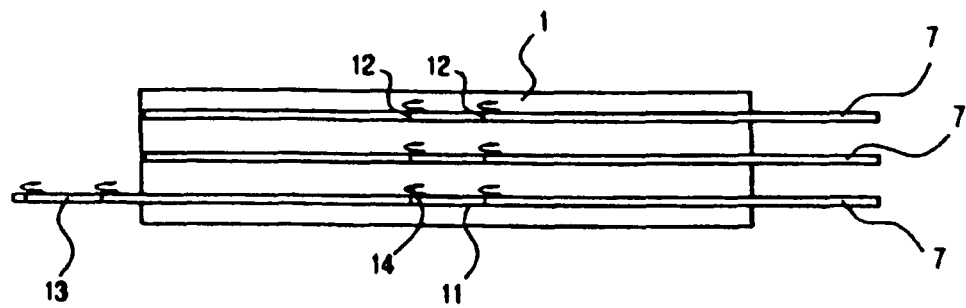
FIG. 5 is a schematic view of the side of the distal extremity showing the disposition of the Intrinsic Fabry-Perot Interferometer (IFPI) sensors.

Referring now to FIG. 5, an alternative embodiment is described in which optical fiber strain sensors 7 comprise Intrinsic Fabry-Perot Interferometers (IFPI). One of the optical fibers is extended and comprises a second IFPI sensor 13 for measuring the temperature of the front end of the distal extremity.

An IFPI comprises a single mode optical fiber having segment having reflectors 12 disposed at either end to define optical cavity 11. The reflectors may comprise semi-reflective mirror surfaces formed in the fiber, or alternatively may comprise two FBGs. Light emitted from a laser diode disposed in console 3 impinges upon the proximal reflector and is partially reflected back at specific wavelengths 14. Light passing through the proximal reflector and impinging upon the distal reflector is also reflected back. The two reflected beams result in constructive and destructive interferences that are detected by a photodetector disposed in console 3.

A variation in strain or temperature changes the optical length of optical cavity 11 and sensor 13, and influences the reflection characteristics from which relative deflections of the optical fibers may be computed. This information in turn permits computation of the force vector imposed upon distal extremity 5 due to contact with the tissue of the wall of the organ or vessel.

Figure 6:
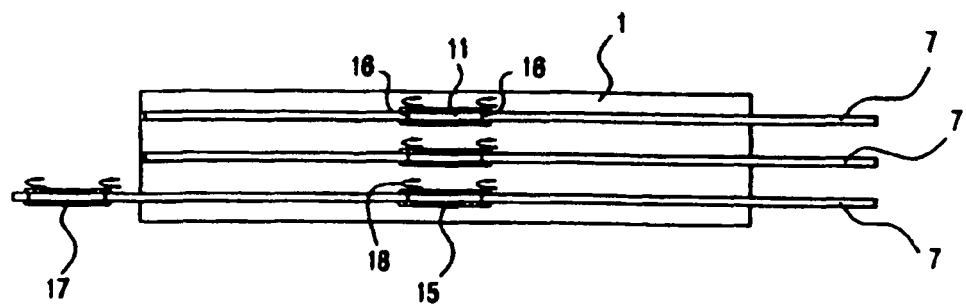
FIG. 6 is a schematic view of the side of the distal extremity showing the disposition of the Extrinsic Fabry-Perot Interferometer (EFPI) sensors.

FIG. 6 illustrates a further alternative embodiment of the distal extremity of catheter 1 and contains three Extrinsic Fabry-Perot interferometer (EFPI) sensors. One of the optical fibers extends beyond the others and comprises a second EFPI sensor 17 to measure the temperature of the front end of the distal extremity. An EFPI sensor comprises optical cavity 11 formed by hollow capillary tube 15 and cut ends 16 of the optical fiber. The hollow capillary tube contains air. Operation of the EPFI is similar to that described above for the IFPI, except that the cut ends of the fiber act as the reflectors to reflect specific wavelengths 18. Light reflected from cut ends 16 result in two beams that constructively and destructively interfere. A variation in strain or temperature changes the length of the optical cavity and influences the reflection characteristics.

Figure 7:
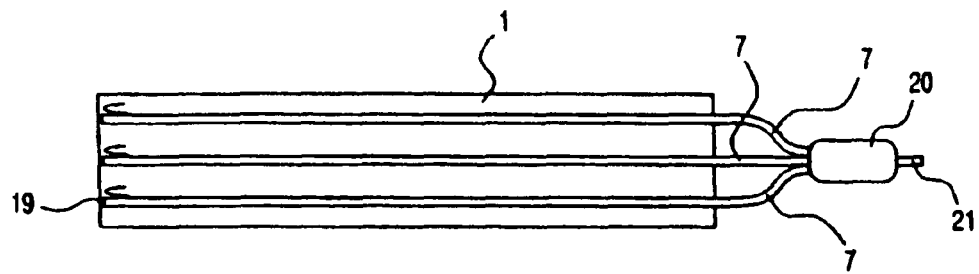
FIG. 7 is a schematic view of the side of the distal extremity showing the disposition of the Michelson interferometer sensors.

FIG. 7 illustrates a further alternative embodiment of the distal extremity of catheter 1, wherein the distal extremity contains three optical fibers 7 that form a Michelson interferometer. Each optical fiber 7 includes reflector 19 at its distal extremity; the fibers are coupled at their proximal ends by optical coupler 20. A wave is injected into fiber 21 from a laser diode disposed in console 3 and is separated by coupler 20 into each of the optical fibers ("arms") of the interferometer. The coupler 20 combines the back reflected light from each arm. Using a coherent or low coherence interferometer, variations in the relative phases of the reflected light from the different fibers are measured to compute the strain experienced by the distal extremity of catheter 1. Based upon the computed strain, the contact force between the distal extremity and the tissue of the organ or vessel wall may be determined.

Figure 8:
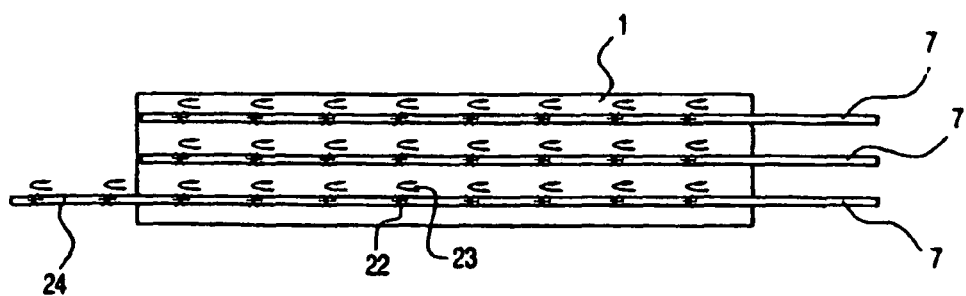
FIG. 8 is a schematic view of the side of the distal extremity showing the disposition of the High Resolution Brillouin sensors.

Referring now to FIG. 8, an embodiment wherein the optical fibers comprise high resolution Brillouin sensors is described. Brillouin sensors use the principle of scattering 22 that is an intrinsic phenomenon of optical fiber. This phenomenon results from the interaction between the light and the phonons (pressure wave) present in the fiber. Wave 23 is backscattered with a shift in optical frequency relative to the injected wave. One of the optical fibers 7 extends beyond the others and comprises a second Brillouin scattering sensor 24 to measure the temperature at the front end of the distal extremity. A variation in strain or temperature changes the shift in optical frequency. Using impulsion, phase modulation or other techniques, it is possible to select different locations 26 along the fiber and to measure the state of strain at these locations.

Figure 9:
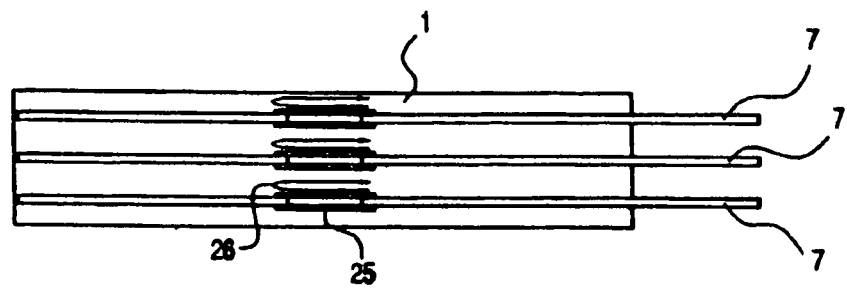
FIG. 9 is a schematic view of the side of the distal extremity showing the disposition of the reflection intensity sensors.
Figure 10:
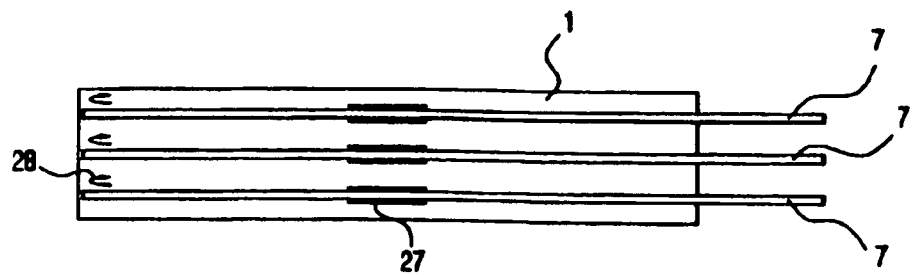
FIG. 10 is a schematic view of the side of the distal extremity showing the disposition of the microbending intensity sensors.

Referring to FIGS. 9 and 10, further embodiments of the present invention are described that employ intensity-type optical fiber sensors. More specifically, FIG. 9 illustrates use of reflection intensity sensors while FIG. 10 illustrates use of microbending intensity sensors.

In FIG. 9, reflection intensity sensors comprise connection zones 25 within optical fibers 7. Under the effect of a strain caused by deformation of the distal extremity, or a temperature variation, connection zones 25 modulate the amplitude of the optical wave 26 that is transmitted and/or reflected. The variation in intensity of the reflected light is measured by apparatus, which is per se known. An additional optical fiber also may be provided to perform temperature measurement.

In FIG. 10, microbending intensity sensors comprise connection zones 27 disposed along the length of optical fibers 7. Connection zones 27 may be obtained by introducing microbendings in the fibers. Under the effect of a strain caused by deformation of the distal extremity, or a temperature variation, connection zones 27 modulate the amplitude of the optical wave 28 that is transmitted and/or reflected. The variation in intensity of the reflected light is measured by apparatus, which is per se known.

Figure 11:
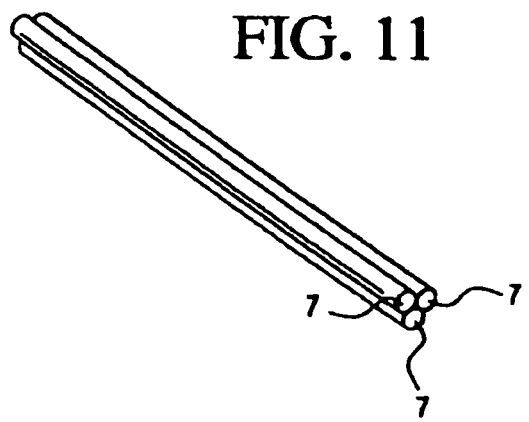
FIG. 11 is a perspective view of three optical fibers in contact with each other.
Figure 12:
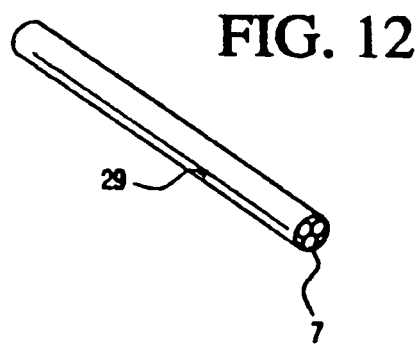
FIG. 12 is a perspective view of three optical fibers in contact with each other and forming an integral part.
Figure 13:
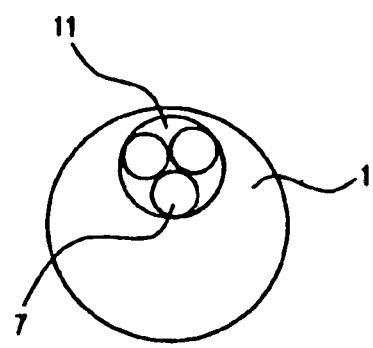
FIG. 13 is a schematic plan view of the distal extremity with the optical fibers of FIG. 6 forming an integral part of the distal extremity.

According to a preferred embodiment, the three optical fibers may be assembled with each other to form an integral part, as depicted in FIG. 11, or embedded with an adhesive or other suitable deformable material to form cylindrical element 29, as depicted in FIG. 12. This arrangement provides a very small solid assembly that may in turn be affixed within a lumen of a catheter of otherwise conventional construction, as depicted in FIG. 13, while also protecting the optical fibers from breakage. In accordance with the principles of the present invention, bundling the fibers as shown in FIGS. 11-13 ensures that all three of the optical fibers are not co-planar.

Figure 14:
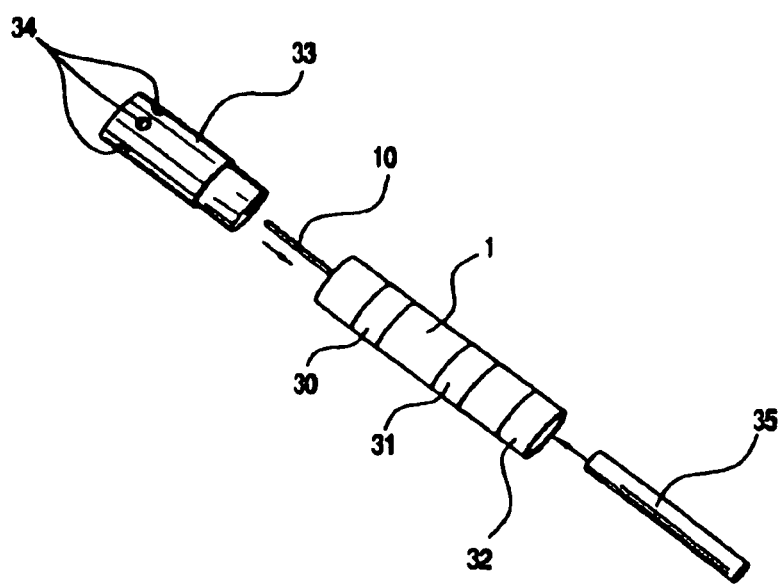
FIG. 14 is an exploded perspective view of the distal extremity of an exemplary catheter constructed in accordance with the present invention.

Referring now to FIGS. 4 and 14, the distal extremity of an exemplary ablation catheter utilizing the load sensing capability of the present invention is described. Catheter 1 includes electrodes 30, 31 and 32 and is coupled to front end 33 having irrigation ports 34. Electrodes 30, 31, 32, 33 are provided according to the function of the specific application for the catheter, for example, endocavity electrocardiogram, radiofrequency ablation, etc. Front end 33 also may be an electrode. Sensor 35 also may be provided that provides three-dimensional positioning of the distal extremity of the catheter, with sensor 35 being based upon electromagnetic, magnetic, electric, ultrasound principles.

The distal extremity of catheter 1 includes at least three fiber optic sensors 9 configured as described hereinabove. One of the optical fibers extends beyond the others and includes, for example, second Bragg grating 10 that serves as a temperature sensor. Bragg grating 10 is received within front end 33 and may be used to compute temperature changes in front end 33 resulting from operation of the electrode. Irrigation ports 34 communicate with one or more channels situated inside the catheter and may be used to deliver a cooling solution, e.g., saline, to the distal extremity of the catheter during operation of the front end electrode to lower the temperature of the front end and control the ablation of tissue.

Although front end 33 is illustratively described as configured for performing radiofrequency ablation, other tissue ablation or treatment end effectors could be used, such as laser, ultrasound, radiation, microwave and others. Furthermore, other therapeutic means such as the injector of medication, stem or other types of cells may also be situated in the head of the catheter.

With respect to FIG. 15, a further alternative embodiment is described wherein a fourth optical fiber is used to measure the temperature of the distal extremity in the vicinity of the other optical fiber strain sensors. Because the material of the distal extremity of catheter 1 may be sensitive to temperature variations, a change of temperature of the distal extremity may result in expansion or contraction of the distal extremity and the embedded optical fibers. This effect may result in computation of a false force vector. Accordingly, fourth optical fiber 7 is slidably disposed in distal extremity 1 so that it is not affected by temperature induced expansion or contraction of the distal extremity of the catheter, and thus provides a reference measurement. If the temperature of the sensor body is known, however, such as by using a fourth optical fiber, thermal expansion or compression of the distal extremity may be compensated in the computation of the force vector.

Referring now to FIG. 16, an alternative embodiment of apparatus utilizing the load sensing system of the present invention is described. Apparatus 40 includes catheter 41 having distal extremity 42 and proximal end 43 coupled to console 45 via cable 44. Construction and operation of components 41-45 is similar to that described above for the embodiment of FIG. 1.

In accordance with one aspect of the present invention, apparatus 40 of FIG. 16 further includes robotic control system comprising controller 46, input and display device 47 and actuator 48. Actuator 48 is coupled to catheter 41 to manipulate the catheter responsive to commands generated by programmed microprocessor 46. Controller 46 is programmed via instructions input via input and display device 47, and the operation of the actuator 48 may be monitored via a display portion that device 47. Controller 46 is coupled to console 45 to receive the output of the load sensing system of the present invention, and to use that information to control manipulation of catheter 41 and actuator 48. Console 45 also may receive an input from controller 46 that is used to determine when the end effector of catheter 41 is operated.

For example, catheter 41 may comprise an electrophysiology catheter designed to map electrical potentials within a patient's heart. In this case, distal extremity 42 may include a series of mapping and ablation electrodes as described herein above with respect to FIG. 14. As described above, previously known methods of mapping electrical potentials within a patient's heart is a time consuming activity, because the clinician determines engagement of with the tissue wall by tactile feedback through the catheter shaft or using impedance measurements.

In accordance with the principles of the present invention, actuator 48 comprises a multi-axis tool capable of advancing and rotating the catheter within the patient's heart. Controller 46 may be programmed to manipulate the catheter until the contact force encountered by distal extremity 42 falls within a predetermined range, as determined via monitoring by console 45. Once the contact force is determined to fall within the predetermined range, the electrical potential may be measured and recorded. Controller 46 then may reposition the catheter as required to map other desired portions of the patient's heart.

Advantageously, because the contact forces applied by the distal extremity can be controlled within desired ranges, the risk of deforming the tissue wall is reduced. Accordingly, if a three dimensional locator system also is provided in the catheter, such as described above, accurate registration of the measured values and the spatial locations of the measurement points may be obtained. The load sensing system of the present invention similarly may be integrated into a treatment system, for example, including the ablation electrode described above with respect to FIG. 14, in which the ablation electrode may be energized to ablate tissue only when the contact force between the distal extremity and the tissue wall exceeds a predetermined minimum value or falls within a predetermined range.

In addition, where distal extremity 42 of catheter 41 is articulable, controller 46 also may provide a signal to console 45 that adjusts the articulation of the distal extremity. In this manner, the load sensing system of the present invention may be configured not only to serve as part of a feedback loop to an external controller, but may itself accept an external control signal that controls operation of an end effector of the catheter.

Referring now to FIG. 17, a further alternative embodiment of an ablation catheter utilizing the load sensing features of the present invention is described. Applicant has observed that some polymers routinely employed in catheter construction, such as polyethylene have a relatively high coefficient of thermal expansion, and a tendency to absorb moisture when exposed to bodily fluids.

Although the dimensional changes resulting from moisture absorption and temperature fluctuations may be small, these environmental factors may introduce artifacts into the forces computed by the apparatus. Moreover, the environmental effects may not be entirely removed by use of an additional optical fiber sensor, such as described with respect to FIG. 15. To address the temperature fluctuation issue, a tube having a low thermal expansion coefficient is disposed in the distal extremity of the catheter in the vicinity of the sensor portions of the optical fibers.

Referring again to FIG. 17, apparatus 50 comprises catheter 51 having proximal end 52 coupled via cable 53 to console 54 having processor 55. Apparatus 50 further comprises distal extremity 56 attached to the distal end of catheter 51 and includes electrode 57 having irrigation ports 58 for cooling the tissue during an RF ablation procedure. Proximal end 52, cable 53, console 54, and processor 55 are similar in design and construction to proximal end 2, cable 4, console 3 and processor 6 of the embodiment of FIG. 1, respectively, which are described in detail above. Apparatus 50 differs mainly in the construction of distal extremity 56, as described below.

Referring now to FIGS. 18 and 19, subassembly 60 disposed within distal extremity 56 of apparatus 50 is described.

Subassembly 60 comprises irrigation tube 61 coupled at proximal end 52 to an infusion port (not shown) and at distal end 62 to irrigation ports 58 of front end 63. Front end 63 preferably is metallic and acts as an ablation electrode, and includes irrigation ports 58 in fluid communication with the interior of irrigation tube 61, so that fluid injected via the infusion port exits through irrigation ports 58.

In FIG. 19, subassembly 60 is disposed within polymeric housing 64, shown partially cut-away for ease of understanding. Optical fiber sensors 65 are arranged around the circumference of irrigation tube 61, preferably spaced 120 degrees apart. Sensors 65 are similar in design and construction to optical fiber sensors 7 of the preceding embodiments, and may be configured to measure strain in any appropriate manner, such as described above and depicted in FIGS. 4-10. Preferably, sensors 65 are Bragg Gratings.

In accordance with one aspect of the invention, irrigation tube 61 preferably comprises proximal portion 66 and distal portion 67. Proximal portion 66 preferably comprises a polymer and more preferably comprises a thin polyimide tube, such as made from KAPTON, available from DuPont, and extends from proximal end 52 to within about 1 cm of distal end 62.

Distal portion 67 couples proximal portion 66 to front end 63. Distal portion 67 preferably is electrically conductive, so as to conduct electrical current to front end 63, for example, by wire 59 coupled to the proximal end of proximal portion 66. Preferably, distal portion 67 is formed of a material having a relatively low coefficient of thermal expansion compared to the rest of catheter 51. Distal portion 67 preferably also has a Young's modulus of elasticity such that, when configured as a thin tube, its axial deformation under an applied load is sufficient to obtain a force resolution with the optical fiber sensors 65 of 1 gram. In a preferred embodiment, distal portion 67 comprises titanium and has a length of approximately 1 cm, whereas the length of the measurement regions of optical fibers 65 is about 4 mm.

Referring now to FIGS. 19 and 20, housing 64 is described in greater detail. Housing 64 preferably comprises a polymer and extends over distal portion 67 of irrigation tube 61 to enclose and protect the measurement regions of optical fiber sensors 65. Housing 64 is bonded to distal portion 67, e.g., with glue or other known attachment means, so that the distal end of the housing does not contact front end 63, but instead forms gap 68.

Housing 64 includes central channel 69 configured to receive distal portion 67 of subassembly 60, and may include grooves 70 on the exterior surface of the housing 64 to accept wires that electrodes on the exterior of housing 64 to proximal end 52. Housing 64 also includes ribs 71 that prevent the housing from directly contacting optical fiber sensors 66. Housing 64 further includes stepped diameter region 72 that facilitates joining the housing to the proximal portion of catheter 51.

As described above, apparatus 50 may be configured to include the capability to deflect the distal extremity of catheter 51 using any of variety of well-known mechanisms, such as pull-wires. More particularly, referring to FIG. 20, an illustrative embodiment of a deflectable catheter shaft suitable for use with subassembly 60 of FIGS. 18 and 19 is described.

Catheter shaft 80 includes handle 81, elongated shaft 82 and deflectable region 83. Shaft 82 preferably comprises braided wire tube 84 embedded within biocompatible polymer 85. Deflectable region 83 preferably comprises flexible catheter material 86 having wire coil 87 embedded with it.

Pull wire 88 is coupled to anchor ring 89 disposed at distal end 90 of deflectable region 83, and extends through coil spring 91 to handle 81. Electrical wires 92, irrigation tube 93 (corresponding to irrigation tube 61 in FIG. 18) and the optical fibers (not shown) extend from handle 81 through anchor ring 89 to the housing of the distal extremity.

Stepped diameter region 72 of housing 64 engages the distal end of catheter shaft 80, so that housing 64 and electrode 57 are disposed distal to anchor ring 89. In this manner, deflection of deflectable region 83 does not impact the strains computed by the optical fiber sensors used to compute contact forces between the distal extremity of the catheter and the wall of the vessel, tissue or organ.

It will be appreciated that other embodiments of an ablation catheter may employ other features discussed elsewhere in this application. For example, an additional sensor may be added to apparatus 50 for measuring temperature using the above-described principles.

In summary, use of optical fiber strain sensors permits computation of a multi-dimensional force vector that arises during contact of the distal extremity of the catheter with the wall of the tissue, organ or vessel. When such information is combined with a 3D positioning sensor, precise mapping may be obtained to permit diagnosis or treatment of tissue at an optimal applied force. The small size of the optical fiber strain sensors and high resolution of measurements obtained by these devices allows highly precise measurements to be obtained even in environments that are humid and subject to electromagnetic interference.

The invention claimed is:

1. Apparatus for ablating tissue in a vessel or organ, the apparatus comprising:
an elongate body having proximal and distal ends and a distal extremity, the distal extremity comprising a deformable material and an ablator configured to ablate tissue upon contact of the ablator and introduction of radiofrequency energy to the ablator, the distal extremity further comprising an irrigation channel having a wall disposed with the distal extremity, the wall comprising a material having a coefficient of thermal expansion lower than a coefficient of thermal expansion of the deformable material;
optical fibers comprising optical contact force sensors affixed to the distal extremity, the optical contact force sensors configured to provide an output corresponding to the value of a contact force between the distal extremity and tissue of the organ or vessel; and
a deflection mechanism disposed in the elongate body, the deflection mechanism configured to deflect the elongate body at a location proximal of the distal extremity.

2. The apparatus of claim 1 further comprising a storage device associated with the elongate body, the storage device containing a force-strain conversion matrix that enables computation of a three-dimensional force vector corresponding to a contact force between the distal extremity and a tissue wall of the organ or vessel.

3. The apparatus of claim 1 further comprising a console having a laser diode, a photodetector and processing logic, wherein the processing logic is programmed to receive an output from the optical strain sensor and to compute the three-dimensional force vector using the force-strain conversion matrix.

4. The apparatus of claim 1 wherein the optical fiber contact force sensors are selected from the group consisting of: a Fiber Bragg Grating optical fiber strain sensor, a Long Period Grating optical fiber strain sensor, an Intrinsic Fabry-Perot Interferometer optical fiber strain sensor, an Extrinsic Fabry- Perot Interferometer optical fiber strain sensor, a Michelson interferometer optical fiber strain sensor, a Brillouin scattering optical fiber strain sensor and an intensity interferometer optical fiber strain sensor.

5. The apparatus of claim 1, wherein a distal part of one of the optical fibers extends distally beyond the other optical fibers and further comprises an additional optical fiber sensor for use in determining temperature.

6. The apparatus of claim 1, wherein the three optical fibers comprise arms of a Michelson or intensity interferometer optical fiber strain sensor and an additional optical fiber extends through the elongate body and distally beyond the other optical fibers and includes an additional optical fiber sensor to measure temperature.

7. The apparatus of claim 1, further comprising a fourth optical fiber having an optical fiber sensor slidably disposed within a lumen of the elongate body to measure a temperature of the distal extremity.

8. The apparatus of claim 1, wherein the ablator further comprises at least one electrode for measuring an electric potential of the tissue of the organ or vessel.

9. The apparatus of claim 8, wherein the console is programmed to measure the electrical potential when the contact force falls within a determined range.

10. The apparatus of claim 1, wherein the elongate body comprises a liquid crystal polymer.

11. The apparatus of claim 10, wherein the liquid crystal polymer includes a moisture resistant coating.

12. The apparatus of claim 9 wherein the ablator is configured to ablate tissue only when the contact force falls within a determined range.

13. The apparatus of claim 1, wherein the irrigation channel conducts radiofrequency energy to the ablator.

14. The apparatus of claim 13 wherein the distal portion comprises titanium.

* * * * *